United States Patent [19]

Braus

[11] 4,326,088

[45] Apr. 20, 1982

[54] PROCESS FOR PREPARING 4,4-DIHYDROXYDIPHENYL ETHER

[75] Inventor: Harry Braus, Cincinnati, Ohio

[73] Assignee: National Distillers & Chemical Corp., New York, N.Y.

[21] Appl. No.: 223,450

[22] Filed: Jan. 8, 1981

[51] Int. Cl.³ .................... C07C 41/26; C07C 43/263
[52] U.S. Cl. .................................. 568/638; 568/567; 568/563
[58] Field of Search ...................... 568/567, 563, 638

[56] References Cited

U.S. PATENT DOCUMENTS 3,462,468  8/1969  Taylor et al. .................. 568/638 X
3,471,576  10/1969  Klesper et al. ................ 568/638 X

*Primary Examiner*—Bernard Helfin
*Attorney, Agent, or Firm*—Kenneth D. Tremain

[57] ABSTRACT

4,4'-dihydroxydiphenyl ether (DHDPE) is prepared by the catalytic oxidation of 4,4'-diisopropyldiphenyl ether to the corresponding dihydroperoxide, the latter being subjected to acid cleavage to provide the desired dihydroxy compound.

5 Claims, No Drawings

PROCESS FOR PREPARING 4,4-DIHYDROXYDIPHENYL ETHER

BACKGROUND OF THE INVENTION

1. Field of the Invention

This invention belongs to the field of processes for preparing diphenyls and, more particularly, to a process for peparing 4,4'-dihydroxydiphenyl ether from the acid cleavage of a hydroperoxide intermediate.

2. Description of the Prior Art

The diphenyl ether,4-4'-dihydroxydiphenyl ether, (DHDPE) which is represented by the structural formula

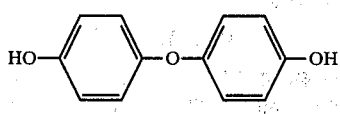

bears a close resemblance to the widely used diphenyl compound, bisphenol A (4,4'-isopropylidenebisphenol), which is represented by the structural formula

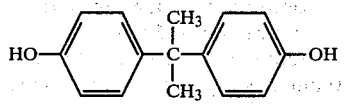

differing from the latter only in the presence of a bridging ether oxygen in place of an isopropylene bridge.

DHDPE, a known compound, despite its attractive properties for numerous applications, has yet to be synthesized in an economical manner and to date has not been commercially manufactured.

An economical synthesis of DHDPE is desirable because it would make commercially available a monomer which confers an unusually high degree of thermal and oxidative stability to compounds and polymers prepared therefrom. Like the extensively employed bisphenol A, DHDPE is useful for preparing polyesters, polyurethanes, polycarbonates, polyethers, mixed polyester/polysulfones and epoxy and phenolic resins. However, unlike bisphenol A, DHDPE conveys to its polymers the properties of a stable aromatic ether. Unlike bisphenol A, there are no deleterious pendant alkyl groups in the structure of DHDPE. In addition to stability, DHDPE convers on its oligomers and polymers a high degree of internal pasticization, an inherent property of polyaromatic ethers. Its oligomers are valuable for extreme pressure lubricants and transformer fluids.

Valuable reactive flame retardant compounds can be made from DHDPE. When fully brominated, the product octabromodihydroxydiphenyl ether can be incorporated as an integral unit of a polymer, in contrast to the unreactive halogenated diphenyl ethers which are at present widely used as flame retardants. Like the very popular decabromodiphenyl ether, DHDPE is substantially nontoxic when incorporated into a polymer.

The brominated derivatives of bisphenol A are reactive flame retardants currently used in high volume. A disadvantage of these is the oxidizable, hence flammable, isopropylidene groups. DHDPE when fully brominated presents only an ether oxygen which enhances flame retardancy properties and contains more bromine than fully brominated bisphenol A. Brominated DHDPE can be converted to nonreactive flame retardants by proper etherification or esterification.

DHDPE was first prepared by the tedious and expensive method of dinitration of the para positions of diphenyl ether, reduction to the corresponding diamine and diazotization and decomposition of the latter with methanol. U.S. Pat. No. 3,290,386 discloses the hydrolysis of 4,4'-dibromodiphenyl ether by excess aqueous caustic in the presence of catalytic quantities of alkaline peroxide and cuprous halide to provide DHDPE. While this procedure is an improvement over the DHDPE synthesis described in German Pat. No. 609,080 which employs methanolic caustic in the presence of copper powder to effect hydrolysis, it has nevertheless not become a commercial reality. Other processes for preparing DHDPE which also have not met with any significant measure of success are described in U.S. Pat. No. 2,739,171 (catalytic dehydration of dihydroxy hydroquinone) and U.S. Pat. No. 3,886,218 (condensation of hydroquinone in an inert organic solvent in the presence of an aluminum silicate catalyst).

SUMMARY OF THE INVENTION

It has now been discovered that DHDPE can be readily and conveniently prepared in good yield by the catalytic oxidation of 4,4'-diisopropyldiphenyl ether to the corresponding dihydroperoxide, the latter then being subjected to acid cleavage to provide the desired compound, DHDPE. These reactions, oxidation and acid cleavage, are believed to proceed overall as shown in the following equations.

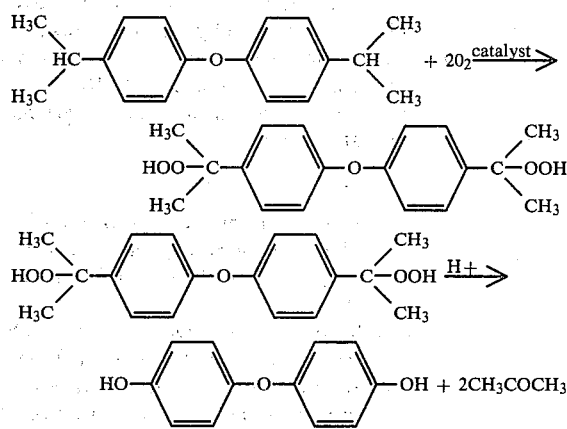

The acetone which is produced as a by-product of the acid cleavage reaction is itself an industrially valuable product and is readily separated from the reaction medium by known and conventional means.

Catalytic oxidation of 4,4'-diisopropyldiphenyl ether to form the corresponding dihydroperoxide, generally in admixture with the monohydroperoxide, can be carried out by any of the known and conventional procedures for preparing hydroperoxides from alkaryl compounds, e.g., those described in U.S. Pat. Nos. 2,680,139; 2,797,249; 2,954,405; 2,989,566; 3,803,243; 3,911,020; 3,953,521; and 3,978,138, each of which is incorporated by reference herein. Briefly stated, such oxidation can be achieved herein by reacting 4,4'-diisopropyldiphenyl ether in the liquid phase at elevated temperatures with oxygen or an oxygen-containing gas such as air, in the presence of an oxidation catalyst such as an alkali or alkaline earth metal oxide, hydroxide, or carbonate, formate, benzoate, e.g., sodium carbonate, sodium hydroxide, calcium hydroxide, copper polyphthalocyanine alone or complexed with an aromatic heterocyclic amine, salts or oxides of heavy metals such as copper (I) chloride, lead oxide, lead naphthenate, and mixtures thereof.

Similarly, acid cleavage of the hydroperoxide can be carried out employing any of the known and conventional procedures including those described in U.S. Pat. Nos. 2,626,281 and 2,628,983, both of which are incorporated by reference herein. In accordance with such known procedures, the hydroperoxide is decomposed at elevated temperature in the presence of acid, preferably strong mineral acid such as sulfuric acid, hydrochloric acid or strong organic acids such as acetic acid, paratoluene sulfonic acid, etc., to provide the desired phenol.

In the foregoing oxidation reaction, quantities of the monohydroperoxide may also be produced which, following acid cleavage, will provide the novel monohydroxy compound, 4-isopropyl-4'-hydroxydiphenyl ether, which can be separated from DHDPE in a known and conventional manner and recycled for oxidation of the unconverted isopropyl group to its hydroperoxide and, subsequent to acid cleavage, to a hydroxy group. In this manner, substantially all of the starting 4,4'-diisopropyldiphenyl ether can be ultimately converted to DHDPE.

The starting phenolic ether compound, 4,4'-diisopropyldiphenyl ether, is a known compound and can be prepared in high yields and at good rates of conversion by the vapor phase catalytic dehydration of para-isopropylphenol over thorium oxide or alumina. Such a process is described in German Pat. No. 1,810,179.

The following examples are illustrative of the process for preparing DHDPE herein:

EXAMPLE 1

This example illustrates the preparation of the dihydroperoxide of 4,4'-diisopropyldiphenyl ether in admixture with the monohydroperoxide derivative of the starting alkaryl ether.

To a 2-necked 200 ml flask was sealed a gas inlet tube at the very bottom having a sintered glass inlet slightly below the body of the flask. The inlet tube was bent to be approximately parallel to the flask and above the oil heating bath. A combination of sodium carbonate and copper phthalocyanine was employed. The total charge to the flask was as follows:

4,4'-diisopropyldiphenyl ether: 20 g
Cumene hydroperoxide (as initiator): 0.5 g
Sodium carbonate: 0.4 g
Sodium stearate (as emulsifier): 0.2 g
Copper phthalocyanine: 0.1 g The charge was heated to 98°-100° C. with stirring as oxygen was passed through the solution. At completion of the reaction, 23.07% total hydroperoxide of 4,4'-diisopropyldiphenyl ether was obtained.

EXAMPLE 2

This example illustrates the preparation of the dihydroperoxide of 4,4'-diisopropyldiphenyl ether, also in admixture with its monohydroperoxide analogue, in a pressure system.

70 g of 4,4'-diisopropyldiphenyl ether and 8.01 ml of 10% aqueous sodium carbonate was charged to a 300 ml stirred autoclave which was pressurized to 150 psig and heated to 120° C. After an initial induction period of a few hours, oxygen began to be consumed in significant quantities indicating rapid progress of hydroperoxide formation. Analysis indicated a yield of total hydroperoxides of 34.24%.

EXAMPLE 3

This example illustrates the acid cleavage of a mixture of the di- and monohydroperoxide derivatives of 4,4'-diisopropyldiphenyl ether produced in accordance with either of the procedures of Examples 1 and 2.

A flask containing 85 ml acetone and 0.2 g sulfuric acid was heated to boiling and 19.45 g of the dihydroperoxide of 4,4'-diisopropyldiphenyl ether admixed with its monohydroperoxide analogue were added dropwise over a period of 20 minutes to the flask. Following such addition, the flask was heated to boiling for another 20 minutes and then cooled. After filtration to recover catalyst, the reaction medium was subjected to distillation for removal of by-product acetone. The remainder of the reaction medium was shown to contain DHDPE admixed with 4-isopropyl-4'-hydroxydiphenyl ether.

What is claimed is:

1. A process for preparing 4,4'-dihydroxydiphenyl ether which comprises reacting 4,4'-diisopropyldiphenyl ether with oxygen to provide the dihydroperoxide derivative of 4,4'-diisopropyldiphenyl ether and thereafter decomposing said dihydroperoxide derivative in the presence of acid to provide 4,4'-dihydroxydiphenyl ether.

2. The process of claim 1 wherein in addition to the dihydroperoxide derivative of 4,4'-diisopropyldiphenyl ether, the reaction of 4,4'-diisopropyldiphenyl ether with oxygen also provides the monohydroperoxide derivative of 4,4'-diisopropyldiphenyl ether.

3. The process of claim 2 wherein the monohydroperoxide derivative of 4,4'-diisopropyldiphenyl ether is decomposed in the presence of acid to provide 4-isopropyl-4'-hydroxydiphenyl ether.

4. The process of claim 3 wherein 4-isopropyl-4'-hydroxydiphenyl ether is reacted with oxygen to provide the hydroperoxide derivative of 4-isopropyl-4'-hydroxydiphenyl ether and said hydroperoxide derivative is decomposed in the presence of acid to provide 4,4'-dihydroxydiphenyl ether.

5. 4,-isopropyl-4'-hydroxydiphenyl ether.

* * * * *